United States Patent [19]

Malz et al.

[11] Patent Number: 5,689,007

[45] Date of Patent: Nov. 18, 1997

[54] PROCESS OF PREPARING PARA SUBSTITUTED PHENYLAMINES

[75] Inventors: Russell Edward Malz, Naugatuck, Conn.; Gerard V. Smith, Carbondale, Ill.; Mark Peter Ferrandino, Danbury, Conn.; Ruozhi Song, Carbondale, Ill.; Chung-Yuan Lin, Orange; Franklin Herbert Barrows, Waterbury, both of Conn.

[73] Assignee: Uniroyal Chemical Company, Inc., Middlebury, Conn.

[21] Appl. No.: 729,703

[22] Filed: Oct. 7, 1996

Related U.S. Application Data

[62] Division of Ser. No. 318,927, Oct. 6, 1994, Pat. No. 5,574,187.

[51] Int. Cl.$^6$ ............................................. C07C 209/36
[52] U.S. Cl. ............................................. 564/402; 564/434
[58] Field of Search ............................................. 564/402, 434

[56] References Cited

U.S. PATENT DOCUMENTS

| | | | |
|---|---|---|---|
| 2,714,614 | 8/1955 | Pitman | 260/571 |
| 2,974,169 | 3/1961 | Newby | 206/576 |
| 3,285,972 | 11/1966 | Young | 260/621 |
| 3,715,397 | 2/1973 | Rylander | 260/575 |
| 3,748,362 | 7/1973 | Klastler | 260/576 |
| 3,953,509 | 4/1976 | Greco | 260/580 |
| 4,034,042 | 7/1977 | Wedemeyer | 260/576 |
| 4,155,936 | 5/1979 | Sturm | 260/576 |
| 4,434,299 | 2/1984 | Chang | 564/396 |
| 4,518,803 | 5/1985 | Batorewicz | 564/410 |
| 4,871,875 | 10/1989 | Nagata | 564/402 |
| 5,420,354 | 5/1995 | Malz et al. | 564/423 |

OTHER PUBLICATIONS

H.E. Heller et al *Nature*, 168 (1951), 909–910.

C.K. Ingold, *Structure and Mechanism of Organic Chemistry*, Cornell University Press, 1953, pp. 622–623.

A. v Baeyer et al, *Justus Liebig's Annalen Der Chemie*, 390, (1912), pp. 139–144 (with translation).

A. v Baeyer et al., *Justus Liebig's Annalen Der Chemie*, 424, (1921), pp. 233, 243–245, 294–296. (with translation).

*Primary Examiner*—Brian M. Burn
*Attorney, Agent, or Firm*—Raymond D. Thompson

[57] ABSTRACT

Processes of preparing para substituted phenylamines, such as, p-phenylenediamines, and particularly, p-aminodiphenylamine. One process involves contacting phenylhydroxylamine with a nucleophilic reagent, such as aniline, in specified proportions and within a specified temperature range, in the absence of oxygen, and in the presence of a homogeneous acid catalyst, such as hydrochloric acid. A second process involves contacting phenylhydroxylamine with a nucleophilic reagent, such as aniline, in the presence of a solid acid catalyst, such as acidic zeolite Y, under reaction conditions.

10 Claims, No Drawings

PROCESS OF PREPARING PARA SUBSTITUTED PHENYLAMINES

This is a division of application Ser. No.08/318,927, filed Oct. 6, 1994 now U.S. Pat. No. 5,574,187.

BACKGROUND OF THE INVENTION

This invention relates to a process of preparing para substituted phenylamines from phenyl-hydroxylamine and nucleophilic reagents, such as amines and alcohols. p-Phenylenediamines, and more specifically, p-aminodiphenylamine are illustrative of the para substituted phenylamines formed in the process of this invention.

Para substituted phenylamines find a variety of utilities depending upon the para substituent. As an example, p-aminodiphenylamine is an important intermediate in the synthesis of rubber antioxidants and antiozonants. Phenylenediamines, particularly $C_{5-10}$ alkyl-substituted derivatives thereof, are also useful in stabilizing rubbers. Para aminophenyl alcohols are useful as chemical intermediates. For example, p-hydroxyaniline is employed in the manufacture of analgesics and antipyretics. Other para substituted phenylamines, such as p-chloroaniline, are useful in the manufacture of dyes, medicinals, and resins.

The syntheses of para substituted phenylamines vary depending upon the para substituent and often require several steps which add undesirably to the production costs.

It is known that phenylhydroxylamine reacts with nucleophilic reagents in the presence of aqueous inorganic acids to yield para substituted phenylamines. See, for example, H. E. Heller et al., Nature, 168, (1951) 909, and E. Bamberger, *Justus Liebig's Annalen der Chemie*, 390, 139–144 (1912); Ibid., 424, 243–245, 294–296 (1921). It is disclosed in these references that phenylhydroxylamine is converted to p-hydroxyaniline in the presence of dilute aqueous sulfuric acid. It is further taught that phenylhydroxylamine reacts with aniline in the presence of dilute aqueous sulfuric acid to yield p-aminodiphenylamine. It is also disclosed that phenylhydroxylamine is converted to o- and p-chloroaniline when the acid employed is hydrochloric acid. Disadvantageously, Bamberger describes multiple by-products, including benzidine, azoxybenzene, and aniline. In a practical sense, there is an added disadvantage. Separation of the acid from the product stream can be expensive. The acid must be neutralized creating a waste salt stream which must be disposed.

It would be advantageous to have a general, one-step process to produce para substituted phenylamines. It would be more advantageous if the process did not require an acid which must be neutralized. Such a process would eliminate the need to dispose of a waste salt stream. It would also be advantageous if high yields of para substituted phenylamines could be obtained. With one or more of these advantages the process would be amenable to commercial application.

SUMMARY OF THE INVENTION

In one aspect, this invention is a process of preparing para substituted phenylamines. The process comprises contacting phenylhydroxylamine with a nucleophilic reagent in the presence of a solid acid catalyst under reaction conditions such that a para substituted phenylamine is formed. Optionally, the process of this invention can be conducted with phenylhydroxylamine substituted with at least one inert substituent such that the correspondingly substituted derivative of a para substituted phenylamine is formed.

Advantageously, the process of this invention produces para substituted phenylamines in one step from phenylhydroxylamine or a substituted derivative thereof. More advantageously, the catalyst employed in the process of this invention is heterogeneous; and therefore, the para substituted phenylamine product stream is easily and inexpensively separated from the catalyst. More advantageously, in preferred embodiments of this invention, described hereinbelow, the process produces para substituted phenylamines in good yield.

In another aspect, this invention is a second process of preparing para substituted phenylamines. The process comprises contacting phenylhydroxylamine with a nucleophilic reagent in the presence of a homogeneous acid catalyst. The molar ratio of nucleophilic reagent to phenylhydroxylamine broadly ranges from about 3 to about 25. The contacting of the phenylhydroxylamine and nucleophilic reagent is conducted at a temperature ranging from about 80° C. to about 100° C., and oxygen is excluded from the process. Under these conditions a para substituted phenylamine is formed in a yield greater than about 15 weight percent. Optionally, this process can be conducted with a phenylhydroxylamine substituted with at least one inert substituent such that the correspondingly substituted derivative of a para substituted phenylamine is formed in a yield greater than about 15 weight percent.

Although the second process of this invention requires the use of a homogeneous acid catalyst which must ultimately be reclaimed or neutralized, the process advantageously produces in preferred embodiments a high yield of para substituted phenylamines.

DETAILED DESCRIPTION OF THE INVENTION

In accordance with the processes of this invention, phenylhydroxylamine is contacted with a nucleophilic reagent in the presence of a heterogeneous solid acid catalyst or a homogeneous liquid acid catalyst to yield para substituted phenylamine. Alternatively, phenylhydroxylamine substituted with at least one inert substituent can replace unsubstituted phenylhydroxylamine in the processes of this invention such that the corresponding inertly substituted derivative of a para substituted phenylamine is formed. In a preferred embodiment of the invention, phenylhydroxylamine is contacted with an amine in the presence of the aforementioned catalysts to yield p-phenylene-diamine. In a more preferred embodiment, phenyl-hydroxylamine is contacted with aniline or substituted aniline in the presence of the aforementioned catalysts to yield p-aminodiphenylamine or a substituted derivative thereof.

Phenylhydroxylamines which are suitable for the processes of this invention include unsubstituted phenylhydroxylamine and substituted derivatives thereof provided that the substituent(s) is(are) inert with respect to the processes of this invention. In addition, the inert substituents(s) should be located at a position other than the para position relative to the hydroxylamine moiety. The para position should remain unsubstituted, because it is this position which is involved in the process with the nucleophilic reagent. Suitable substituents include linear and branched $C_{1-10}$ alkyl moieties, amino (—$NH_2$), hydroxyl, halo, keto [—C(O)R], ether (—OR), and ester moieties [—OC(O)R], wherein the R substituent is preferably a $C_{1-10}$ alkyl or a $C_{6-10}$ aryl or alkaryl group. Non-limiting examples of suitable substituted phenylhydroxylamines include methylphenylhydroxylamine, ethylphenylhydroxylamine, isopropylphenylhydroxylamine, aminophenylhydroxylamine, hydroxyphenylhydroxylamine and the like. Preferably, the phenylhydroxylamine is unsubstituted or substituted with a $C_{1-10}$ alkyl moiety. More preferably, the phenyl-hydroxylamine is unsubstituted phenylhydroxylamine.

A nucleophilic reagent is also required for the process of this invention. The term "nucleophilic reagent" is meant to include ions or molecules that are capable of donating a pair of electrons to an atomic nucleus, in this case the para carbon atom of the phenylhydroxylamine, so as to form a covalent bond. Suitable nucleophiles include ammonia, water, aliphatic alcohols, phenols, halides in the acid or tetraalkylammonium forms, and primary and secondary aliphatic amines, alicyclic amines, aryl and alkaryl amines. Preferred amines are represented by the formula $R^1_2NH$, wherein each $R^1$ is independently hydrogen, a $C_{1-20}$ aliphatic, a $C_{4-8}$ alicyclic, or a $C_{6-15}$ aryl or alkaryl moiety. Non-limiting examples of suitable aliphatic amines include ethylamine, diethylamine, propylamine, dipropylamine, butylamine, dibutylamine, and analogous higher homologues. Suitable examples of alicyclic amines include cyclopentylamine and cyclohexylamine. Suitable examples of aryl and alkaryl amines include aniline, toluidine, dimethylaniline, ethylphenylamine, propylphenylamine, and isopropylphenylamine. Preferred aliphatic alcohols include $C_{1-20}$ aliphatic alcohols, suitable examples of which include ethanol, propanol, isopropanol, butanols, pentanols, hexanols, heptanols, octanols, and higher homologues of these. Suitable phenols include phenol and $C_{1-10}$ alkyl substituted phenols, such as cresol. Suitable halides include the tetraalkylammonium chlorides, bromides, and iodides, such as, tetraethylammonium bromide and tetramethyl-ammonium chloride, as well as, the hydrogen halides, such as, hydrogen chloride, hydrogen bromide, hydrogen iodide and hydrogen fluoride. The preferred nucleophilic reagents are amines of the formula $R^1_2NH$ wherein each $R^1$ is independently hydrogen, a $C_{1-20}$ aliphatic moiety, a $C_{4-8}$ alicyclic, or a $C_{6-15}$ aryl or alkaryl moiety. The more preferred nucleophilic reagents are amines of the formula $R^1_2NH$ wherein each $R^1$ is independently hydrogen, a $C_{1-5}$ alkyl moiety, or a $C_{6-10}$ phenyl or alkyl-substituted phenyl moiety. The most preferred nucleophilic reagent is aniline.

Any molar ratio of nucleophilic reagent to phenylhydroxylamine is suitable for the processes of this invention provided that a para substituted phenylamine is obtained as a product. When the nucleophilic reagent is a liquid under the process conditions, the nucleophilic reagent may also act as a solvent for the process. Consequently, the amount of nucleophilic reagent employed relative to phenylhydroxylamine is generally large. Suitable molar ratios of nucleophilic reagent to phenylhydroxylamine are generally equal to or greater than about 2. Preferably, the molar ratio of nucleophilic reagent to phenyl-hydroxylamine ranges from about 2 to about 25. When a solid acid catalyst is employed in the process of this invention, the most preferred molar ratio of nucleophilic reagent to phenylhydroxylamine lies between about 2 and about 10. When a homogeneous acid catalyst is employed in the process of this invention, the most preferred molar ratio of nucleophilic reagent to phenylhydroxylamine lies between about 3 and about 20. Below the preferred lower ratio the conversion of the phenylhydroxylamine may be too low. Above the preferred upper ratio, the excess nucleophilic reagent may be costly to handle.

Alternatively, if the nucleophilic reagent is a solid, it may be desirable to conduct the processes in the presence of an inert solvent. The term "inert" means that the solvent does not interfere with the processes of this invention and is unreactive towards the reagents, products, and catalysts. Suitable solvents include polar-organic solvents, such as dimethylsulfoxide, dimethyl acetamide and nitrobenzene. If a solvent is employed, the quantity can vary depending upon the solubilities of the specific reagents and products involved. One skilled in the art can readily determine an acceptable quantity of solvent. As a general rule, the ratio of the moles of solvent to moles of phenylhydroxylamine is greater than about 5 but lower than about 20, and is preferably between about 8 and about 12.

The catalyst employed in the processes of this invention is any homogeneous or heterogeneous acid catalyst capable of condensing the aforementioned phenylhydroxylamines and nucleophilic reagents into para substituted phenylamines. Suitable homogeneous acid catalysts will dissolve in the liquid phase reaction mixture. Such catalysts include concentrated inorganic acids, such as hydrochloric, hydrobromic and sulfuric acids, as well as organic acids, such as trifluoroacetic acid. The term "concentrated" is taken to mean a concentration, generally in an aqueous medium, of greater than about 6M. Preferably, the concentration is greater than about 8M, and more preferably, is between about 10M and about 12M.

Suitable heterogeneous solid acid catalysts include the metal oxides of Groups IVA (Ti, Zr, Mr) and VA (V, Nb, Ta) of the Periodic Table, as well as the oxides of aluminum and silicon, and mixtures thereof. Non-limiting examples of this group include silica, alumina, silica-aluminas, titania, zirconia, and niobium oxide. Preferred among this group are silica-aluminas, silicas, and aluminum oxides.

Other suitable solid acid catalysts include acidic clays, such as montmorillonite and Filtrol™ brand acid clay. Also suitable are acidic crystalline microporous aluminosilicate zeolites, including, zeolites X, Y, ZSM-5, and mordenite. Preferred among this group are zeolites Y and ZSM-5 in the acid form. Even more preferred are acidic Y zeolites having a silica to alumina molar ratio between about 5 and about 50, more preferably, between about 5 and about 30. Inasmuch as many zeolites are purchased or synthesized in the alkali or alkaline earth form, it may be necessary to convert the zeolite to its acid form. Techniques for doing this are well known to the skilled artisan. Typically, the metal ion form of the zeolite is stirred in an aqueous solution of an inorganic acid, such as hydrochloric or nitric acid, until all or a portion of the metal ion sites have been ion-exchanged for the acid form.

Other suitable solid acid catalysts include insoluble acidic cationic exchange resins, such as, poly(perfluoroalkylene) sulfonic acid, available as Nation® brand; or macroporous sulfonated crosslinked polystyrenes or the corresponding styrene/acrylate copolymers available as Amberlite® brand; as well as polysulfonated siloxanes. Preferred among this group is Nafion® brand poly(perfluoroalkylene)sulfonic acid.

Combinations, such as physical mixtures, of two or more of the aforementioned solid acid catalysts may also be employed in the process of this invention.

When a solid acid catalyst is employed in the process of this invention, it is preferred that the process is conducted in the absence of a homogeneous liquid acid, even if the liquid acid is functioning as a source of a nucleophile. In such instances, alternative sources of the desired nucleophile are preferred.

The process of this invention may be conducted in any standard reactor, such as, a stirred batch reactor, a fixed-bed continuous flow reactor, a fluidized bed reactor, or a transport reactor. Typically, the phenylhydroxylamine is in the liquid or liquid phase, and the nucleophilic reagent is in the liquid or gaseous phase, preferably, the liquid phase. Usually, air is excluded from the reactor by flushing or pressurization with a non-reactive gas, such as, nitrogen, helium, argon, or hydrogen. The presence of air leads to lower product yields.

Any operable process conditions may be employed provided that the desired para substituted phenylamine product is formed. Preferred process conditions vary depending upon the particular catalyst, phenylhydroxyl-amine, and nucleophile, and depending upon the concentrations of these materials. Usually, the process temperature ranges between about 10° C. and about 170° C., and preferably, between about 70° C. and about 100° C. When a homogeneous acid catalyst is employed, the more preferred temperature lies between about 80° C. and about 100° C. In a batch reactor the pressure is autogenous, and the reaction time is typically 3 hr or less to achieve nearly complete conversion of the phenylhydroxylamine. In a fixed bed, continuous flow reactor, the pressure can vary from subatmospheric to superatmospheric, but preferably, is slightly superatmospheric, for example, from about 1.5 to about 5.0 atmospheres, so as to exclude air from leaking into the reactor.

The quantity of solid acid catalyst employed in the process of this invention can range from a catalytic amount to more than a stoichiometric amount relative to the phenylhydroxylamine, provided that the desired para substituted phenylamine product is formed. In a batch reactor, the catalyst is employed in an amount preferably ranging from about 0.1 to about 20 parts per 1 part by weight phenylhydroxylamine, more preferably, from about 0.5 to about 15 parts per 1 part by weight phenylhydroxylamine. In a continuous, fixed-bed reactor the weight hourly space velocity determines the relative ratio of reactants to catalyst as well as the residence time of the reactants in the reactor. For the purposes of this invention, the weight hourly space velocity (WHSV), defined as the grams of liquid feedstream per gram catalyst per hr, or simply $hr^{-1}$, ranges from about $0.01\ hr^{-1}$ to about $100\ hr^{-1}$.

The quantity of homogeneous liquid acid catalyst employed in the process of this invention can range from a catalytic amount to more than a stoichiometric amount relative to the phenylhydroxyl-amine, provided that the desired para substituted phenylamine product is formed. Preferably, however, the molar ratio of homogeneous acid catalyst to phenyl-hydroxylamine ranges from about 0.7 to about 20. More preferably, the molar ratio of homogeneous acid catalyst to phenylhydroxylamine ranges from about 1 to about 10, most preferably, from about 1 to about 5. Generally, the nucleophilic reagent and the concentrated acid are loaded into the reactor, and then a solution containing the phenylhydroxylamine is added slowly. The rate of addition of the phenylhydroxylamine ranges from about 0.05 ml/min to about 1.20 ml/min, and preferably, from about 0.10 ml/min to about 0.20 ml/min.

When phenylhydroxylamine, optionally substituted with at least one inert substituent, is contacted with a nucleophilic reagent in the presence of the solid acid catalyst or homogeneous acid catalyst, as described hereinbefore, a para substituted phenylamine is produced. The product may be represented by the general formula:

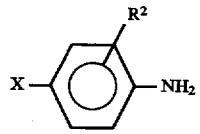

wherein $R^2$ is hydrogen, or alternatively, can represent one or more inert substituents mentioned hereinbefore in connection with the phenylhydroxylamine reactant; and X is hydroxy, halo, alkoxy, phenoxy, or amino of the formula $—NR^1{}_2$, wherein each $R^1$ is independently hydrogen, a $C_{1-20}$ aliphatic, $C_{4-8}$ alicyclic, or $C_{6-15}$ aryl or alkaryl moiety. Preferably, X is amino wherein each $R^1$ is independently hydrogen, or a $C_{1-20}$ aliphatic, $C_{4-8}$ alicyclic, or $C_{6-15}$ aryl or alkaryl moiety, and the product is broadly classified as a p-phenylenediamine. More preferably, X is amino wherein each $R^1$ is independently hydrogen, a $C_{1-5}$ alkyl, or $C_{6-10}$ phenyl or alkyl-substituted phenyl moiety. Most preferably, $R^2$ is hydrogen, X is $—NR^1{}_2$, one $R^1$ is hydrogen, and the other $R^1$ is phenyl, and the product is p-aminodiphenylamine represented by the formula:

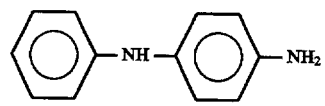

Isolation of the para substituted phenylamine product is accomplished using techniques well known to those skilled in the art. In the process employing a solid acid catalyst, the heterogeneous catalyst is simply filtered from the product stream. In the process employing a homogeneous acid catalyst, the acid is neutralized with base, e.g., ammonia, and the organics are extracted from the resulting salt mixture. Typically, unreacted nucleophilic reagent and any solvent are separated from the organic products by distillation. The crude para substituted phenylamine may be used as is or further purified by known methods, such as fractional distillation, liquid chromatography, or recrystallization.

For the purposes of this invention, the term "conversion" refers to the weight percentage of phenylhydroxylamine or inertly substituted phenylhydroxylamine which reacts to form products. The conversion varies depending upon the reactants, the form of the catalyst, and the process conditions, such as temperature, pressure, and flow rate. Within the preferred temperature range, as the temperature increases the conversion generally increases. Within the preferred space velocity range, as the space velocity increases the conversion generally decreases. Typically, the conversion of phenylhydroxylamine is greater than about 80 weight percent, preferably, greater than about 90 weight percent, more preferably, greater than about 97 weight percent.

For the purposes of this invention, the term "yield" refers to the weight percentage of a particular product, notably para substituted phenylamine, in the product stream. Typically, the yield of para substituted phenylamine is greater than about 3 weight percent, preferably greater than about 15 weight percent, and most preferably, greater than about 35 weight percent. In the preferred embodiment comprising the condensation of aniline and phenylhydroxylamine over a solid acid catalyst, the yield of p-aminodiphenylamine is typically greater than about 3 weight percent, preferably, greater than about 8 weight percent, and more preferably, greater than about 15 weight percent. In another preferred embodiment comprising the condensation of aniline and phenylhydroxylamine in the presence of a homogeneous acid catalyst, the yield of p-aminodiphenylamine is typically greater than about 15 weight percent, preferably, greater than about 30 weight percent, and more preferably, greater than about 50 weight percent.

The following examples are provided to illustrate the processes and claims of this invention, but should not be construed as limiting their scope. All percentages in the examples are weight percent unless otherwise indicated.

EXAMPLES 1–15

The condensation of phenylhydroxylamine with aniline is carried out in the presence of a series of solid acid catalysts according to the following general procedure. A 50 ml wide-mouth reaction flask is fitted with a thermometer, condenser, mechanical stirrer, and a reservoir attached through an inlet port. The reservoir and inlet port are fitted with side arms connected with rubber tubing for the introduction of helium gas.

A solid acid catalyst and aniline (20 or 30 ml) are added to the reaction flask, as specified in Table I. A solution of phenylhydroxylamine (2.2 g) in solvent (20 or 40 ml) is placed in the reservoir. The entire reactor system is flushed with helium gas before heating, and a slow stream of helium is maintained during the reaction. The reaction mixture is heated with agitation to the desired reaction temperature. At the reaction temperature, the solution of phenylhydroxylamine is added over a period of time, shown in the table, into the reaction flask at a constant rate via a metering pump. After addition of the solution, the heating mantle is removed, and the reaction mixture is cooled to room temperature under a continuous flow of helium. The reaction products are analyzed by high performance liquid chromatography (HPLC) with the results shown in Table I.

TABLE I[1]

Condensation of Phenylhydroxylamine with Aniline

| Ex. | Solid Acid/g | Addn. Time (min) of PHA soln. | T (°C.) | Wt. % Yield[12] p-ADPA |
|---|---|---|---|---|
| 1 | TiO$_2$/9.8 | 60 | 150 | 4.5 |
| 2 | SiO$_2$/10 | 90 | 150 | 16.5 |
| 3 | Al$_2$O$_3$/10 | 90 | 150 | 1.1 |
| 4 | Nb$_2$O$_5$/10 | 90 | 100 | 6.3 |
| 5 | Al$_2$O$_3$—SiO$_2$/10 | 90 | 100 | 14.8 |
| 6 | Filtrol™ clay[2]/8.5 | 90 | 80 | 14.3 |
| 7 | Filtrol™ clay[2]/8.3 | 90 | 73 | 17.5 |
| 8 | ASP[3]/9.8 | 120 | 100 | 15.5 |
| 9 | Nafion™[4]/4.9 | 90 | 100 | 7.7 |
| 10 | Amberlyst™[5]/10.0 | 90 | 120 | 12.4 |
| 11 | Mor[6]/10 | 90 | 150 | 14.0 |
| 12 | Y[7]/9.5 | 90 | 90 | 26.0 |
| 13 | Y[8]/10 | 90 | 100 | 17.6 |
| 14 | Y[9]/9.4 | 90 | 100 | 16.9 |
| 15 | Fer[10]/17 | 90 | 150 | 13.2 |
| 16 | Kaolin[11]/9.5 | 30 | 100 | 13.8 |
| 17 | Kaolin[11]/9.7 | 180 | 90 | 13.9 |

[1]Each experiment employs the indicated amount of solid acid in 20 ml of aniline, with the exception of Ex. 5, 10, and 11 which uses 30 ml of aniline. To the mixture are added 2.2 g of phenylhydroxylamine in 20 ml of aniline (40 ml in Expt 15) over the indicated time and at the indicated temperature.
[2]Filtrol™ acid clay, dried in Ex. 6 at 105° C.
[3]Polysulfonated siloxane (ASP)
[4]Nafion™ perfluorosulfonic acid membrane, acid form
[5]Amberlyst™ sulfonated styrene/acrylate copolymer
[6]Acid Mordenite zeolite
[7]Ultrastable acid zeolite Y, SiO$_2$/Al$_2$O$_3$ 11.5, dried at 105° C.
[8]Ultrastable acid zeolite Y, SiO$_2$/Al$_2$O$_3$ 5.2
[9]Ultrastable acid zeolite Y, SiO$_2$/Al$_2$O$_3$ 30.0
[10]Ferrierite, SiO$_2$/Al$_2$O$_3$/K$_2$O/Na$_2$O = 85/9/6/2
[11]Kaolin acid clay modified with zeolite Y
[12]As determined by external standard HPLC analysis It is seen in Table I that a variety of solid acid catalysts, including silica, alumina, silica-alumina, titania, niobia, sulfonated cationic exchange resins, acid clays, and acid zeolites, catalyze the condensation of phenylhydroxylamine and aniline to para aminodiphenylamine. Best yield at 26 percent is with acid zeolite Y.

EXAMPLES 18–24

The condensation of phenylhydroxylamine with aniline is conducted in the presence of a series of solid acid catalysts according to the following general procedure. The solid acid catalyst is charged into a glass reactor fitted with an inlet port and outlet port, as well as a septum seal. The reactor system is flushed with argon or hydrogen gas. The temperature of the reactor is raised to the desired reaction temperature. Aniline is injected all at once into the reactor. Then, a solution containing phenylhydroxylamine is injected into the reactor via a metering pump. After all of the phenylhydroxylamine is added, the reactor is cooled to room temperature. An aliquot (0.1 ml) of the reaction mixture is removed from the reactor by syringe, neutralized with ammonia (0.5 ml), diluted with methanol to 5 ml, and analyzed by HPLC. Process conditions and results are set forth in Table II.

TABLE II[1]

Condensation of Aniline with Phenylhydroxylamine

| Ex. | Solid Acid/g | T (°C.) | PHA Solution PHA (g) | PHA Solution PhNH$_2$ (ml) | Wt. % Yield p-ADPA[6] |
|---|---|---|---|---|---|
| 18 | Nafion™[2]/1.5 | 165 | 2.20 | 10 | 4.2 |
| 19 | Nafion™[2]/1.5 | 150 | 0.70 | 3 | 7.6 |
| 20 | SiO$_2$/NaHSO$_4$/1 | 170 | 0.70 | 3 | 14.4 |
| 21 | HY[3]/1 | 160 | 0.70 | 3 | 20.3 |
| 22 | HY[3]/1 | 160 | 0.70 | 3[5] | 6.8 |
| 23 | HY[3]/2 | 155 | 1.40 | 6 | 11.4 |
| 24 | HZSM-5[4]/1 | 155 | 0.57 | 3 | 8.3 |

[1]Each experiment uses the indicated amount of solid acid in the following amount of solvent: 10 ml aniline (Ex. 18, 21, 23, 24), 7 ml aniline (Ex. 20), 10 ml dimethylsulfoxide (Ex. 19, 22). To this mixture is added the indicated solution of phenylhydroxylamine (PHA) in aniline (PhNH$_2$) at a rate of 0.1 ml/min and at the shown temperature.
[2]Nafion™ perfluorosulfonic acid membrane
[3]Zeolite Na-Y (Linde, Union Carbide) ion-exchanged with NH$_4$Cl, dried at 110° C./6 hr, calcined at 500° C./1.5 hr
[4]Acid zeolite ZSM-5
[5]Lithium chloride (0.1 g) is added to the solution.
[6]As determined by external standard HPLC analysis It is seen from Table II that a variety of solid acid catalysts are capable of catalyzing the condensation of aniline and phenylhydroxylamine to para aminodiphenylamine. The solid acid catalysts include silica, polysulfonated styrene/acrylate copolymer, and acid zeolites, such as zeolites HY and HZSM-5. Best yield at 20 percent is with acid zeolite Y.

EXAMPLES 25–32

The condensation of phenylhydroxylamine and aniline is carried out in the presence of a series of solid acid catalysts according to the following general procedure. A solid acid catalyst is charged into a hydrogenation reactor attached to a shaker, and the reactor system is flushed with argon or hydrogen gas. The temperature of the reactor is raised to 85° C. Aniline is injected all at once into the reactor. Then, a solution containing phenylhydroxylamine is injected into the reactor via a metering pump. After all of the phenylhydroxylamine is added, the reactor is cooled to room temperature. An aliquot (0.1 ml) of the reaction mixture is removed from the reactor by syringe, neutralized with ammonia (0.5 ml), diluted with methanol to 5 ml, and analyzed by HPLC. Process conditions and results are set forth in Table III.

TABLE III[1]

Condensation of Aniline with Phenylhydroxylamine

| Ex. | Solid Acid/g | Wt. % Yield[5] p-ADPA |
|---|---|---|
| 25 | Filtrol ™[2]/2 | 7.7 |
| 26 | HY[3]/2 | 10.0 |
| 27 | HZSM-5[4]/2 | 1.5 |
| 28 | Filtrol ™[2]/2 | 10.4 |
| 29 | SiO$_2$/NaHSO$_4$/2 | 2.1 |
| 30 | Filtrol ™[2]/2 | 12.0 |
| 31 | Montmorillonite clay/2 | 7.9 |
| 32 | Fithian Illite clay/2 | 4.7 |

[1]Each experiment uses the indicated amount of solid acid in 4.0 ml aniline, with the exception of Ex. 29 which uses 8.0 ml aniline. To this mixture at 85° C. is added a solution containing 0.15 g phenylhydroxylamine in 2 ml aniline.
[2]Filtrol ™ acid clay (Fluka), dried in Ex. 30 at 500° C.
[3]Acid zeolite Y
[4]Acid zeolite ZSM-5
[5]As determined by external standard HPLC analysis It is seen that a variety of acid clays and acid zeolites are capable of catalyzing the condensation of aniline and phenylhydroxylamine to para aminodiphenylamine. Best yield at 12 percent is with acid clay calcined at 500° C.

EXAMPLES 33–41

The condensation of phenylhydroxylamine with aniline in the presence of a homogeneous, concentrated liquid acid is conducted according to the following general procedure. The reaction flask is flushed with argon for 20 minutes. Aniline is introduced to the flask via syringe through a septum. Concentrated liquid acid is introduced into the flask slowly with stirring. The temperature of the resulting mixture is raised to the desired reaction temperature. A solution of phenylhydroxylamine in solvent is prepared and injected into the reaction flask via a syringe or high pressure pump. At varying intervals an aliquot (0.1 ml) of the reaction mixture is removed by syringe, neutralized with ammonia (0.5 ml), diluted with methanol to 5 ml volume, and analyzed by HPLC. Process conditions and results are listed in Table IV.

It is seen that concentrated hydrochloric and hydrobromic acids are capable of catalyzing the condensation of aniline and phenylhydroxylamine to para aminodiphenylamine. Best yield is about 51 percent with concentrated hydrochloric acid.

What is claimed is:

1. A process of preparing para substituted phenylamines comprising contacting phenylhydroxylamine, optionally substituted with at least one inert substituent, with a nucleophilic reagent, the molar ratio of nucleophilic reagent to phenylhydroxylamine ranging between about 2 and about 25, the contacting of the phenylhydroxylamine and nucleophilic reagent being conducted in the absence of oxygen and in the presence of a homogeneous acid catalyst at a temperature ranging from about 80° C. to about 100° C. such that a para substituted phenylamine, optionally correspondingly substituted with at least one inert substituent, is formed in a yield greater than about 15 weight percent.

2. The process of claim 1 wherein the phenylhydroxylamine is unsubstituted phenylhydroxylamine.

3. The process of claim 1 wherein the nucleophilic reagent is selected from the group consisting of ammonia, water, $C_{1-20}$ aliphatic alcohols, phenols, halides, and amines having the formula $R^1{}_2NH$ wherein each $R^1$ may independently be a hydrogen, $C_{1-20}$ aliphatic, $C_{4-8}$ alicyclic, or $C_{6-15}$ aryl or alkaryl moiety.

4. The process of claim 1 wherein the nucleophilic reagent is aniline.

5. The process of claim 1 wherein the homogeneous acid is selected from the group consisting of hydrochloric, hydrobromic, and trifluoroacetic acids.

6. The process of claim 1 wherein the para substituted phenylamine is represented by the formula:

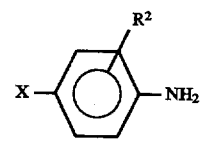

wherein $R^2$ is hydrogen or at least one $C_{1-10}$ alkyl moiety, and X is selected from hydroxy, halo, $C_{1-20}$ alkoxy,

TABLE IV

Condensation of Aniline with Phenylhydroxylamine[1]

| Ex. | PhNH$_2$ (mmoles) | Conc. Acid/ml | T (°C.) | Rate ml/min | Solution PHA (mmoles) | Solvent[2] (ml) | Wt. % Yield p-ADPA[4] |
|---|---|---|---|---|---|---|---|
| 33 | 440 | HCl/20 | 85 | 0.20 | 43 | DMSO/20 | 34.2 |
| 34 | 110 | HCl/5 | 100 | 0.13 | 25 | ROH/10 | 22.1 |
| 35 | 220 | HCl/10 | 90 | 0.13 | 22 | A/10 | 26.7 |
| 36 | 220 | HCl/15 | 85 | 0.10 | 40 | A/10 | 39.0 |
| 37 | 110 | HCl/9 | 100 | 0.20 | 17 | A/10 | 41.5 |
| 38 | 220 | HCl/15 | 100 | 0.20 | 19 | A/10 | 51.2 |
| 39 | —[3] | —[3] | 100 | 0.22 | 19 | A/20 | 23.9 |
| 40 | 220 | HBr/15 | 100 | 0.11 | 19 | A/10 | 15.5 |

[1]To the indicated millimoles of aniline (PhNH$_2$) containing the shown amount of concentrated acid catalyst (10 M HCl or 6 M HBr) is added the indicated solution of phenylhydroxylamine (PHA)° at the temperature and rate of addition shown. Conversion of PHA is 100 percent in all examples.
[2]Solvents: DMSO = dimethyl sulfoxide, ROH = cyclohexanol, A = aniline.
[3]Dimethylacetamide, 20 ml, containing 23.5 g of aniline hydrochloride (PhNH$_2$.HCl) is employed.
[4]As determined by external standard HPLC analysis.

phenoxy, and amino of the formula —NR$^1_2$ wherein each R$^1$ is independently a C$_{1-20}$ aliphatic, C$_{4-8}$ alicyclic, or C$_{6-15}$ aryl or alkaryl moiety.

7. The process of claim 6 wherein X is amino and the para substituted phenylamine is a p-phenylenediamine.

8. The process of claim 7 wherein the para substituted phenylamine is p-aminodiphenylamine represented by the formula:

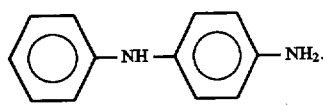

9. The process of claim 8 wherein the yield of para aminodiphenylamine is greater than about 30 weight percent.

10. A process of preparing p-aminodiphenylamine comprising contacting phenylhydroxylamine and aniline, the molar ratio of aniline to phenylhydroxylamine being between about 3 and about 20, the contacting being conducted in the absence of oxygen and in the presence of concentrated hydrochloric acid at a temperature in the range from about 80° C. to about 100° C. such that p-aminodiphenylamine is produced in a yield greater than about 50 weight percent.

* * * * *